(12) United States Patent
Knoepfle et al.

(10) Patent No.: US 10,123,832 B2
(45) Date of Patent: Nov. 13, 2018

(54) SURGICAL FORCEPS SYSTEM

(71) Applicant: Stryker European Holdings I, LLC, Kalamazoo, MI (US)

(72) Inventors: Christian Knoepfle, Donaueschingen (DE); Karl Greiner, Müehlheim (DE); Manfred Schmuck, Müehlheim (DE); Friedhelm Beyersdorf, Freiburg (DE); Rainer Günther Leyh, Würzburg (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 369 days.

(21) Appl. No.: 14/821,276

(22) Filed: Aug. 7, 2015

(65) Prior Publication Data
US 2016/0038200 A1 Feb. 11, 2016

Related U.S. Application Data

(60) Provisional application No. 62/035,024, filed on Aug. 8, 2014.

(51) Int. Cl.
*A61B 17/82* (2006.01)
*A61B 17/88* (2006.01)
*A61B 17/84* (2006.01)

(52) U.S. Cl.
CPC .......... *A61B 17/82* (2013.01); *A61B 17/8866* (2013.01); *A61B 17/842* (2013.01)

(58) Field of Classification Search
CPC . A61B 17/28; A61B 17/2804; A61B 17/2812; A61B 17/2816; A61B 17/282; A61B 17/2833; A61B 17/2841; A61B 17/82; A61B 17/823; A61B 17/826; A61B 17/84; A61B 17/842; A61B 17/8866; A61B 2017/2837; A61B 2017/2845
USPC .................................................... 606/96, 207
See application file for complete search history.

(56) References Cited

U.S. PATENT DOCUMENTS

| | | | |
|---|---|---|---|
| 4,444,180 A * | 4/1984 | Schneider | A61B 17/1714 606/96 |
| 4,896,668 A | 1/1990 | Popoff et al. | |
| 5,318,566 A | 6/1994 | Miller | |
| 5,391,181 A * | 2/1995 | Johnson | A61B 17/282 606/207 |

(Continued)

FOREIGN PATENT DOCUMENTS

| | | |
|---|---|---|
| DE | 3146634 C2 | 3/1984 |
| DE | 102005021236 A1 | 11/2006 |

(Continued)

*Primary Examiner* — Eric S Gibson
(74) *Attorney, Agent, or Firm* — Lerner, David, Littenberg, Krumholz & Mentlik, LLP (57) ABSTRACT

A surgical instrument for fixing bone fragments is provided. The surgical instrument comprises a positioning member with two pad holding portions, two pad members each having a bone contacting surface and each configured to be releasably held at one of the pad holding portions of the positioning member so that the bone contacting surfaces of the two pad members face each other, and two guiding channels configured to receive a flexible elongated member, each guiding channel being formed in a region between the bone contacting surface of one of the pad members and the associated pad holding portion.

25 Claims, 8 Drawing Sheets

(56) References Cited

U.S. PATENT DOCUMENTS

| | | | |
|---|---|---|---|
| 5,697,933 A * | 12/1997 | Gundlapalli | A61B 17/1714 606/206 |
| 5,746,757 A * | 5/1998 | McGuire | A61B 17/0482 606/139 |
| 5,797,916 A | 8/1998 | McDowell | |
| 5,797,919 A * | 8/1998 | Brinson | A61B 17/8866 606/105 |
| 6,033,429 A | 3/2000 | Magovern | |
| 6,159,217 A * | 12/2000 | Robie | A61B 17/155 606/207 |
| 6,287,307 B1 * | 9/2001 | Abboudi | A61B 17/8061 606/105 |
| 6,315,780 B1 * | 11/2001 | Lalonde | A61B 17/282 606/105 |
| 8,257,359 B2 * | 9/2012 | Burkhart | A61B 17/1657 606/87 |
| 8,267,957 B1 * | 9/2012 | Silver | A61B 17/2833 606/105 |
| 8,597,327 B2 | 12/2013 | Stone et al. | |
| 8,728,087 B2 * | 5/2014 | Soliman | A61B 17/158 269/3 |
| 8,747,410 B2 * | 6/2014 | Claypool | A61B 17/158 606/102 |
| 8,936,628 B2 * | 1/2015 | Anderson | A61B 17/0401 606/216 |
| 9,113,969 B2 * | 8/2015 | Niederberger | A61B 17/8019 |
| 9,675,400 B2 * | 6/2017 | Katrana | A61B 17/8866 |
| 2002/0082604 A1 * | 6/2002 | Abdelgany | A61F 2/4644 606/79 |
| 2004/0176779 A1 * | 9/2004 | Casutt | A61B 17/1757 606/102 |
| 2005/0021087 A1 | 1/2005 | Koseki | |
| 2008/0177297 A1 * | 7/2008 | Steiner | A61B 17/28 606/205 |
| 2012/0123428 A1 * | 5/2012 | Berberich | A61B 17/17 606/96 |
| 2013/0338719 A1 | 12/2013 | Madjarov | |
| 2013/0345762 A1 * | 12/2013 | Dell'Oca | A61B 17/8866 606/324 |
| 2014/0031882 A1 * | 1/2014 | Schmuck | A61B 17/68 606/324 |
| 2015/0005779 A1 * | 1/2015 | Tepic | A61B 17/1714 606/96 |
| 2015/0073440 A1 * | 3/2015 | Li | A61B 17/0483 606/144 |
| 2015/0313640 A1 * | 11/2015 | O'Daly | A61B 17/56 606/86 R |
| 2015/0374425 A1 * | 12/2015 | Hashmi | A61B 17/8866 606/105 |
| 2016/0038200 A1 * | 2/2016 | Knoepfle | A61B 17/82 606/324 |

FOREIGN PATENT DOCUMENTS

| | | |
|---|---|---|
| EP | 0242267 B1 | 11/1989 |
| EP | 0631493 B1 | 2/1998 |
| EP | 0847730 A1 | 6/1998 |
| EP | 0958786 A2 | 11/1999 |
| EP | 1080693 A1 | 3/2001 |
| EP | 1732460 B1 | 5/2010 |
| JP | 3886010 B2 | 2/2007 |
| WO | 2001097676 A2 | 12/2001 |
| WO | 2006119885 A1 | 11/2006 |
| WO | 2012027025 A2 | 3/2012 |

* cited by examiner

SURGICAL FORCEPS SYSTEM

CROSS REFERENCE TO RELATED APPLICATION

The present application claims the benefit of the filing date of U.S. Provisional Patent Application No. 62/035,024 filed on Aug. 8, 2014, the disclosure of which is hereby incorporated herein by reference.

FIELD OF THE INVENTION

The present disclosure generally relates to a surgical instrument for fixing bone fragments. In particular, a surgical instrument and a method for fixing bone fragments are described, as well as a surgical kit assembly comprising the surgical instrument, a pad member and a carrier member.

BACKGROUND OF THE INVENTION

To promote the healing process of a fragmented or split bone, it has been known to exert an external force on the bone fragments by tightly clamping them together. For doing so, flexible elongated members such as wires or threads can be used which are tensioned around the bone fragments.

For example, during chest or heart surgery, it is known to split the sternum into two halves by means of a longitudinal section. The sternum halves need then to be joined again, for example, by arranging a wire around the sternum halves in a circumferential manner, so as to surround a cross-sectional area thereof. The cross-sectional area extends typically transverse to the longitudinal section through the sternum. Afterwards, the wire is tensioned by connecting and twisting the free ends thereof.

Furthermore, it has been known to arrange protector pads between the wire and an adjacent surface of the respective bone fragments. The protector pads avoid that the wire cuts into the bone surface when tensioning it, thus causing damage to the bone.

U.S. Pat. No. 6,287,307 generally discloses an apparatus and a method for clamping the split bone sections of a sternum. For doing so, protector pads in form of sternal plates are arranged in opposite configuration at the split sternum halves. The sternum plates are provided with spikes which are driven into outer side surfaces of the sternum halves by means of a forceps. The sternum plates are hence directly fixed at the bone fragments in a first step. Afterwards, a surgeon can guide and tension a circumferential wire around the sternum plates and the bone fragments arranged therebetween.

U.S. Pat. No. 8,597,327 generally discloses a method and apparatus for securing a fractured or sectioned sternum by means of a flexible member construct forming circumferential loops around the sternum halves. In addition, protector members are provided for guiding and fixing said flexible member construct around the sternum halves.

PCT Appln. No. WO 2012/027025 generally discloses a method for closing a sternum with help of adhesives. The adhesives may also be applied in contact regions between the sternum halves and an additionally provided circumferential wire to form a protective layer similar to the known protector pads.

There is a need for a surgical instrument for fixing bone fragments which can be reliably operated and limits unnecessary damage to the bone fragments.

SUMMARY OF THE INVENTION

According to one aspect of the present invention, a surgical instrument for fixing bone fragments is provided, comprising a positioning member with two pad holding portions, two pad members each having a bone contacting surface and each configured to be releasably held at one of the pad holding portions of the positioning member so that the bone contacting surfaces of the two pad members face each other, and two guiding channels configured to receive a flexible elongated member, each guiding channel being formed in a region between the bone contacting surface of one of the pad members and the associated pad holding portion.

The positioning member may be configured with a handling portion which a surgeon can grasp and/or operate for placing the pad members at bone fragments to be fixed. The pad holding portions of the positioning member are preferably spaced apart from the handling portion. In one variant, the handling portion and pad holding portion are arranged at opposite ends of the positioning member. The pad holding portions may comprise pointed or sharp end sections having a reduced width. They may be configured with curved end sections and/or generally extend an angle to adjacent sections of the positioning member.

The pad members may be configured as separate or individual members and preferably as separate one-piece members. Alternatively, the pad members may be connected to one another and/or form part of a protector pad arrangement comprising the two pad members. Generally, the pad members may be configured to protect an adjacent surface of the bone fragments from damage, for example, when tensioning a flexible elongated member around said bone fragments. For doing so, the pad members may be configured to be at least partially positioned between the flexible elongated member and an adjacent or associated bone fragment. Furthermore, the pad members may at least partially be configured of a plastic or polymer material, such as silicon, PCU or the like. In one design, the pad members are at least partially formed of PEEK. Other than that, any bio-compatible material may be used for forming the pad members.

The bone contacting surfaces of the pad members are generally configured to be arranged adjacent to a surface of the bone fragments and, preferably, to directly abut against it. The bone contacting surfaces can have any shape or form and may define a rectangular or oval as well as a planar or curved area. In one embodiment, at least one of the bone contacting surfaces is provided with grooves and/or recesses. Also, at least one of the bone contacting surfaces may comprise a flexible portion which is, for example, formed by means of a specifically selected material or an at least locally reduced material strength. The bone contacting surfaces can comprise at least one inwardly inclined or curved end portion which may be formed by a protrusion.

Generally, the pad members can be arranged within the surgical instrument so as to be positioned opposite to one another. For example, the pad members can be in one common plane. In one embodiment, the pad members are arranged within the surgical instrument in a mirror-symmetrical manner.

It is noted that in the present or any further aspect, the surgical instrument may as a whole be configured in a mirror-symmetrical manner. Alternatively, any or several of the specific features of the surgical instrument, such as the positioning member, the pad holding portions, the two guiding channels as well as the pad members or the bone contacting surfaces thereof may be configured mirror-symmetrically to one another. On the other hand, at least the pad holding portions, the two guiding channels, the pad members or the bone contacting surfaces thereof may also be configured different from one another, (e.g., with regard to the shape, dimensions or material).

The flexible elongated member can comprise or be formed by a wire, a thread or the like.

The guiding channels for receiving said flexible elongated member may be configured to at least partially surround and/or accommodate the flexible elongated member after it has been inserted. The guiding channels can be configured to guide and arrange the flexible elongated member around the bone fragments to be fixed. Also, the guiding channels can be configured to guide and arrange the flexible elongated member in such a manner that the pad members or at least their bone contacting surfaces are at least partially arranged between the flexible elongated member and an adjacent surface of the bone fragments.

With regard to the above described application scenario of sternal closure, the surgical instrument may in the present or any further aspect be configured to position the pad members with help of the positioning member at different sternum halves. In particular, it may be provided that the surgical instrument is configured to arrange the pad members in a cross-sectional plane extending substantially transverse to or orthogonal to a sectional plane through a longitudinally split sternum. Also, the guiding channels may be formed so as to at least partially extend within said cross-sectional plane and in a circumferential direction around the sternum halves. The guiding channels can further be configured to guide the flexible elongated member around the sternum halves so as to form a circumferential wire for clamping the sternum halves together.

The guiding channels can have a straight, curved, bent or inclined course or comprise single sections describing a respective course and/or a plurality of sections having different courses from one another. Preferably, the guiding channels extend with a continuous course along a straight or curved longitudinal axis.

In one realization, the guiding channels extend at least partially along the associated bone contacting surface. Accordingly, the course of the guiding channels may include a directional or vectorial component extending in parallel to the bone contacting surfaces. The course described by the guiding channels may include vectorial components extending both in parallel as well as transverse to the bone contacting surfaces. The absolute value of the parallel vectorial component preferably exceeds that of the transversal one. Likewise, the guiding channels may generally extend circumferentially along the bone contacting surfaces. The above described aspects according to this paragraph may be valid for at least part of or for more than half of the length of the guiding channels.

According to one possible design, the guiding channels extend at least approximately parallel to the associated bone contacting surface. Preferably, the guiding channels extend at a distance to the bone contacting surfaces and/or do not intersect them.

According to a further aspect, the bone contacting surfaces each confine an outer circumference of a clamping space located between the bone contacting surfaces, and each guiding channel has at least two openings which are arranged at different positions along the circumference of the clamping space. As exemplified above with reference to sternal closure, the bone contacting surfaces may generally be arranged so as to at least partially surround or extend in a cross-sectional area of a fragmented bone. Also, the bone contacting surfaces may be configured to clamp the bone fragments by exerting a clamping or pressure force acting within a cross-sectional area of the fragmented bones. Accordingly, the circumference of the clamping space as confined by the bone contacting surfaces may equally extend circumferentially around and/or confine a cross-sectional area of the fragmented bones.

The openings of the guiding channels can open to an outside of the surgical instruments and/or be arranged on an outer surface thereof. Furthermore, they may be arranged so as to be manually accessible from outside for inserting the flexible elongated member into the guiding channels. In one design, the openings comprise a guiding structure, such as a funnel-shaped section or rounded edges, to facilitate insertion of the flexible elongated member. Preferably, the openings are arranged in outermost circumferential regions or at opposite circumferential ends of, for example, the pad holding portions and/or the pad members.

In one embodiment of the surgical instrument, the bone contacting surfaces have a circumferential as well as a transversal extension, with the circumferential extension exceeding the transversal extension, and each guiding channel has at least two openings which are arranged at different positions along the circumferential extension. In other words, the bone contacting surfaces may confine an area which is marked by a long (circumferential) extension and a shorter (transversal) extension.

The longer circumferential extension may represent the longest extension of the bone contacting surfaces in any direction. In one example, the bone contacting surfaces define a substantially rectangular or oval area and the circumferential extension corresponds to the longest axis within said area. In case of a substantially rectangular bone contacting surface, the axis determining the circumferential extension may extend at least approximately in parallel with the longer sides of the rectangular area defined by said bone contacting surface. Also, the circumferential extension may be defined as the extension along a longitudinal or length axis of an associated guiding channel.

The transversal extension can be defined as extending orthogonally to the circumferential extension. With regard to sternal closure, the transversal extension may substantially extend in parallel to the sectional plane through the sternum, whereas the circumferential extension may extend in a cross-sectional plane of and around the sternum.

As explained above, the openings of the guiding channels may thus be positioned at opposite and/or outermost circumferential end regions of, for example, the pad holding portions and/or pad members.

The guiding channels can be configured with a substantially constant cross-section along their length or at least with a substantially constant shape of the cross-section, such as a circular or rectangular shape. Also, the guiding channels may be configured to, in at least a section, surround the flexible elongated member on three sides, wherein said sides may be arranged orthogonally to one another. Likewise, the guiding channels and/or the respective wall surfaces thereof may be configured to confine a cross-sectional area of at least 90° for extending around the flexible elongated member and preferably a cross-sectional area of at least 120°, 180° or 270°. In other words, the guiding channels may confine a cross-sectional area for extending around the flexible elongated member and include openings in said cross-sectional area of, for example, at most 90°, 180° or 270°. The angular values referred to above may be measured with respect to a geometric center of the cross-sectional area.

In a further aspect, the guiding channels comprise at least one section or portion which is configured with a closed cross-section. Preferably, the guiding channel is provided with a closed cross-section along its complete length or, in other words, defines a fully enclosed tunnel structure through the surgical instrument. Alternatively, the guiding channels may be provided with a closed cross-section at least in the region of the pad members and/or for more than half or more than three quarters of their length.

The guiding channels may have a length of at least 5 mm. The length of the guiding channel may refer to the length of extension through the surgical instrument or, in other words, the length along which the guiding channel can guide and accommodate the elongated member. Also, the length of the guiding channel may refer to the length of the course of the guiding channel when extending through the surgical instrument along a longitudinal axis. Also, the length may refer to the length of the guiding channel when extending between its two openings.

Preferably, the length of the guiding channel exceeds the largest extension or dimension of the pad members, for example, in a circumferential direction. Generally, the guiding channel can have a length from 10 mm to 100 mm, for example, 30 mm to 60 mm.

According to a further aspect, the largest cross-sectional extension of the guiding channels is below 5 cm. This may refer in particular to those sections of the guiding channels having a closed cross-section. In other words, the cross-section along the length of the guiding channel may be configured so as to not extend for more than 5 cm in any direction. Accordingly, the largest cross-sectional extension of the guiding channels can be between 1 mm and 20 mm, for example 2 mm to 10 mm or preferably 2 mm to 4 mm. In one example, the guiding channel is comprises a substantially circular cross-section, such that the largest cross-sectional extension is defined by the diameter of a respective circle.

One possible design of the surgical instrument includes that the guiding channels are at least partially formed in the pad members. In other words, the guiding channels may at least partially extend through and/or be confined by an associated pad member. The guiding channels can, for example, be fully defined by or extend solely through the pad members for at least a section along their course. In other words, the pad members may fully define at least a section of the guiding channels along their lengths. In these sections, the guiding channels can generally be configured with an open or closed cross-section.

The pad members may equally confine at least part of a cross-sectional area of at least a section of the guiding channels. For example, the pad members can form at least part of a wall surface of the guiding channels, wherein said wall surface together with further portions of the surgical instrument confines a respective section of the guiding channel.

Likewise, the guiding channels can at least partially be formed in the positioning member. Preferably, the guiding channels are formed in an associated pad holding portion of the positioning member. Similar to above, the positioning member may thus fully define a length or longitudinal section of the guiding channel or at least partially confine a cross-sectional area thereof, for example, by means of providing a partial wall surface for forming the guiding channels.

In one example, the positioning member and preferably the pad holding portions thereof define a section of the guiding channels along their lengths, wherein the guiding channels comprise an open cross-section within said section. Preferably, said cross-sections are arranged so as to open inwardly towards a respectively opposite bone contacting surface. This may allow the elongated flexible member to slide out of the guiding channel sections formed in the pad holding portions when removing the positioning member from the bone fragments.

In one aspect, the guiding channels are formed in both of the pad members as well as the positioning member and preferably in both of a pad member and an associated pad holding portion.

According to one design, the guiding channels comprise an elongated through-hole. Preferably, the guiding channels or at least the longest section thereof can be formed by as a respective elongated through-hole. The ends of the through-hole may form openings of the guiding channels for inserting the elongated member therein. The through-hole can comprise or be formed by a channel or passage extending through the surgical instrument and having a substantially circular cross-section. Likewise, the guiding channels may comprise at least one elongated recess.

In a further aspect, the positioning member is configured to move at least one of the bone contacting surfaces towards the other to exert a clamping force. The movement of the contacting surfaces may comprise at least one of a linear and rotating or pivoting movement. The positioning member can be configured to move both bone contacting surfaces simultaneously towards each other and, preferably, move both bone contacting surfaces by same amounts.

In this connection, the positioning member may further be configured to arrange the bone contacting surfaces in a defined distance to each other and to hold said distance upon exerting a clamping force. Accordingly, the positioning member can move the bone contacting surfaces in discrete steps or in a stepless manner towards each other and clamp bone fragments arranged therebetween. For holding the clamping distance, the positioning member can comprise a locking mechanism, such as a ratchet mechanism, a screw mechanism, a snap-fit connection, lockable gears or the like.

According to one variant, the positioning member is a forceps and the pad holding portions are formed in tip regions of the forceps. The positioning member can be configured as a repositioning forceps or reduction forceps. The tip regions may be located in an outermost region with regard to a rotational joint by means of which the forceps can be opened and closed. The forceps may further comprise a handling portion and the rotational joint of the forceps may be located between the tip regions and the handling portion. In other words, the handling portion and tip regions can be located at opposite ends of the positioning member.

The pad members can be releasably held at the pad holding portions by means of at least one of a form-fit and a press fit. Accordingly, the pad member can be held at the pad holding portions by means of a snap-in connection or a similarly releasable locking mechanism. To achieve the form-fit and/or press fit, at least one of the pad member and associated holding portion may be configured with a deformable section. Preferably, said deformable section is at least partially elastically deformable.

In one embodiment, at least one of the pad members is configured with a mounting portion to be releasably inserted into a receiving section of an associated pad holding portion. The mounting portion may comprise or be formed by a protrusion of the pad member, whereas the receiving section of the pad holding portion may comprise or be formed by a recess. The receiving section and mounting portion may at least partially be configured with corresponding shapes. For example, the receiving section may be provided as a recess within the pad holding portion which is correspondingly shaped to a protrusion-like mounting portion of the pad member.

To realize the above-mentioned form-fit and/or press fit, at least one the mounting portion and receiving section can comprise an elastically deformable section. In one variant, the receiving section is made of a stiff material and the mounting portion comprises an elastically deformable section which is deformable upon inserting the mounting portion into the receiving section. The elastically deformable section of the mounting portion can comprise or be formed by a bendable section of material. Also, the elastically deformable section can be produced by providing a cut or recess in the mounting portion adjacent to a lateral edge region thereof.

In this context, the mounting portion and the bone contacting portion can be arranged on opposite sides of the pad member. Alternatively or additionally, the mounting portion and bone contacting surface can be arranged on adjacent sides of the pad member. According to one aspect, the bone contacting surface faces inwardly so as to abut against a surface of the bone fragments, whereas the mounting portion faces away from said bone fragments and towards an associated pad holding portion of the positioning member.

In one embodiment of the surgical instrument, at least one of the pad members has a generally curved main part with the bone contacting surfaces arranged on an inner side of the curved main part and the mounting portion arranged on an outer side of the curved main part. The terms "inner" and "outer" may generally refer to radially inner and radially outer sides of the curved main part. For example, assuming that the curved main part forms part of a respectively closed circular or oval cross-section, the inner side faces to the inside of said cross section, whereas the outer side faces outwardly.

According to a further aspect, the surgical instrument can comprise at least one securing member for temporarily securing at least one of the pad members at the positioning member and for releasing the pad member from the positioning member upon operating the securing member. The securing member may represent or provide a release mechanism for selectively holding and/or locking the pad member at the positioning member. The securing member can generally be configured as a movable part or section of the positioning member and be operable with help of a button, a lever or the like. The securing member can, when in an actuated state, lock or engage the pad member so as to produce a form-fit and/or press fit.

The securing member can comprise or be formed by a removable member, such as a removable pin. The latter may be insertable into the positioning member and, preferably, into a section of the pad holding portions. Upon insertion, the removable pin can at least partially enclose, engage or obstruct at least a part of a pad member so as to avoid a release thereof. Upon removing the removable pin, the pad member can be released, for example, to remain at the bone fragments to be fixed.

The securing member can comprise or be formed by a spring member which may bias the pad members against an associated pad holding portion, for example for producing a form-fit and/or press fit. The spring member may be arranged at the pad member and/or an associated pad holding portion.

According to a further aspect, there is provided a surgical kit assembly, comprising a flexible elongated member, for example in form of a wire or thread, and a surgical instrument according to any of the aspects and variants discussed above.

The surgical kit assembly can further comprise a carrier member for releasably carrying the pad members prior to holding them at the positioning member. The carrier member can thus be provided as a temporary carrier or holding means for the pad members prior to performing a surgical intervention with help of the surgical instrument. A surgeon can use the carrier member to provide the pad members to the positioning member or, in other words, for grasping or picking-up the pad members from the carrier member by means of the positioning member.

In a further aspect, a method for fixing bone fragments is provided, wherein said method comprises the steps of: a) releasably holding a pad member at each of two pad holding portions of a positioning member; b) positioning the pad members at bone fragments by means of the positioning member, such that bone contacting surfaces of the pad members contact the bone fragments; c) arranging a flexible elongated member in guiding channels, each guiding channel extending in a region between the bone contacting surface of one of the pad members and an associated pad holding portion; d) tensioning the flexible elongated member around said bone fragments, such that the pad members are at least partially arranged between the flexible elongated member and the bone fragments; e) releasing the pad members from the positioning member; and f) removing the positioning member.

With regard to step b), it may be provided that the pad members are positioned at different bone fragments which need to be clamped to one another. For example, it may be provided that the pad members are arranged at different sternum halves for performing a sternal closure procedure. Furthermore, it may be provided that a clamping force is exerted and held by the positioning member after performing step b), for example, by means of a positioning member configured as a forceps and/or provided with a locking mechanism as discussed above.

With regard to step c), it may be provided that the flexible elongated member is inserted into a first opening of a first guiding channel, wherein said opening faces outwardly and/or towards a surgeon. Afterwards, the flexible elongated member can be guided circumferentially along the bone fragments and arranged in a region facing away from the surgeon. With regard to sternal closure, this region may correspond to a region of the sternum facing inwardly toward the inner organs of a patient. Afterwards, the elongated member can be received in the guiding channel of the second pad member. The flexible elongated member may then be guided back towards a region facing the surgeon.

In other words, according to step c), it may be provided that the flexible elongated member is guided circumferentially around the bone fragments and, preferably, from one pad member to the other. After performing step c), free ends of the flexible elongated member may be arranged adjacent to one another and/or on a same side or in a same region of the bone fragments. Preferably, this side or region corresponds to a side or region facing the surgeon and/or being oriented towards the outside of the patient's body (e.g. the outwardly facing surface of a sternum).

With regard to step d), the flexible elongated member can be tensioned by twisting free ends thereof or by generally reducing a circumferential length of the flexible elongated member along or around the bone fragments.

Furthermore, it can be provided that the flexible elongated member is guided around the bone fragments without abutting against or contacting any bone surfaces. Rather, the elongated member can be arranged so as to contact only the pad members arranged in between the bone fragments and the elongated member. Also, the elongated member may be arranged to not contact any further elements in at least a section, for example, when extending from one pad member to the other.

With regard to step e), it can be provided that the pad members are released manually, for example, by pulling on the flexible elongated member or by operating a release mechanism and/or securing member according to one of the aspects discussed above. Also, the pad members may be released by opening the forceps.

Furthermore, with regard to step f), it may be provided that the clamping forces which can be provided in or after step b) are substantially upheld until the positioning member is finally removed. For example, step f) may involve releasing the locking or clamping mechanism of the positioning member prior to actually removing it.

The sequence of the single steps as described above can generally be changed. Also, the steps may at least partially overlap each other. For example, the clamping forces of the positioning member can also directly be released after step d). Furthermore, the flexible elongated member can at least partially be arranged in at least one of the guiding channels prior to step b).

In a further aspect, a pad member for fixing bone fragments is provided, the pad member having a bone contacting surface and a mounting portion which are arranged on opposite sides of the pad member, the mounting portion including at least one protrusion comprising an elongated recess, the elongated recess forming a guiding channel section for receiving an elongated member.

The pad member may generally be configured according to any of the aspects and variants as previously discussed. For example, the elongated recess may be formed as a through-hole. Furthermore, the pad member and in particular the mounting portion may be provided with an elastically deformable section for producing a form-fit and/or press fit upon inserting them into a pad holding portion of a positioning member as previously discussed.

In a further aspect, a carrier member is provided for releasably holding two pad members for fixing bone fragments, the pad members each having a bone contacting surface and a mounting portion which are arranged on opposite sides of the pad member, the pad members being arranged on opposite sides of the carrier member with each of the bone contacting surfaces facing an associated fixing portion of the carrier member.

As previously discussed, the carrier member may generally be provided to temporarily hold the pad members prior to arranging them at a positioning member for positioning them at bone fragments. The pad members may be arranged at the carrier member in positions, so that they can simultaneously be picked-up or connected to the pad holding portions of a forceps. Accordingly, the pad members can be arranged mirror-symmetrically at the carrier member and/or in a common circumferential plane thereof. The bone contacting surfaces may be closely arranged at or abut against the fixing portions of the carrier member. In one aspect, the bone contacting surface are shielded from outside when arranged at the carrier member. Also, the bone contacting surfaces can be received in a receiving section formed at the fixing portions. The receiving section may be formed by recess. The recess can be correspondingly shaped to an outer shape or outline of the bone contacting surfaces.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

In the following, embodiments of a surgical instrument for fixing bone fragments, as well as a carrier member and surgical assembly kit will be described. The same reference numerals will be used to denote the same or similar structural features.

Figures 1, 2:
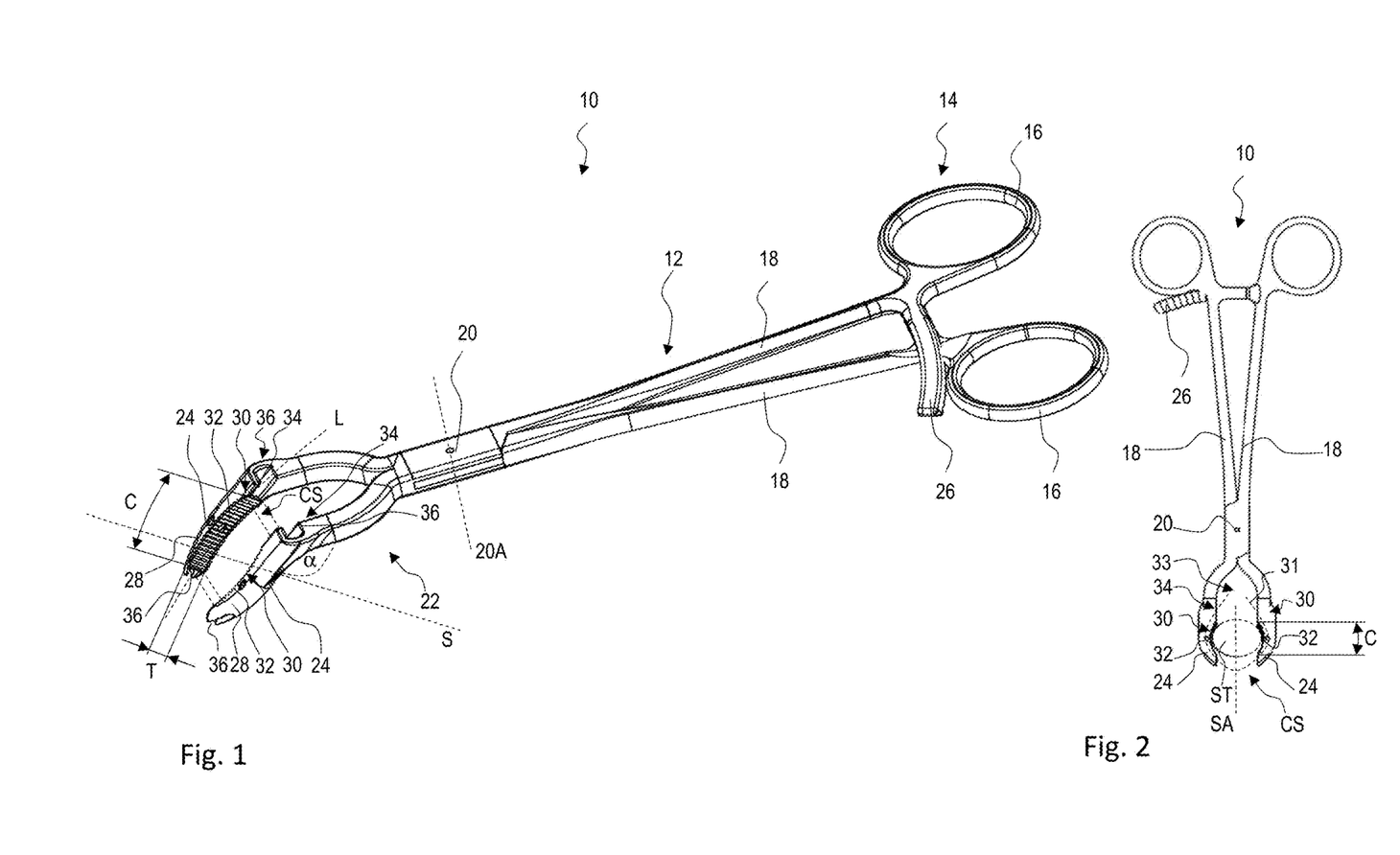
FIG. 1 shows a perspective view of a first embodiment of a surgical instrument of the present invention comprising a positioning member and two pad members.
FIG. 2 shows a schematic top view of the surgical instrument according to FIG. 1, with bone fragments being received in a clamping space of the surgical instrument.

FIG. 1 shows a perspective view of a surgical instrument 10 according to a first embodiment. The surgical instrument 10 comprises a positioning member 12 being formed as a forceps. The forceps 12 comprises a handling portion 14 including circular portions 16 for inserting, in a well-known manner, fingers therein and operating two arms 18 of the forceps 12 to rotate around a rotational joint 20. The rotational joint 20 thus defines a rotational axis 20A for opening and closing the forceps 12.

The forceps 12 further comprises a tip region 22 with two pad holding portions 24. The pad holding portions 24 are each associated with one of the arms 18 of the forceps 12, so as to jointly rotate around the rotational joint axis 20A.

The forceps 12 further includes a ratchet mechanism 26 to, in a well-known manner, move the arms 18 in discrete steps relative to one another about the rotational joint axis 20A. Also, the ratchet mechanism 26 acts as locking mechanism which avoids an undesired opening of the forceps 12 after closing it by a desired amount of steps.

The pad holding portions 24 are configured as elongated end sections of the tip region 22 and extend in an angled manner with respect to the adjacent sections of the arms 18.

As indicated in FIG. 1, the respective angle α between the pad holding portions 24 and the adjacent sections of the arms 18 amounts to approximately 120°. Furthermore, the pad holding portions 24 are provided with lower curved end sections 28 which are inclined and curved towards a respectively opposite pad holding portion 24.

The surgical instrument 10 further comprises two pad members 30 each being releasably held at an associated pad holding portion 24. Note that in the illustration according to FIG. 1, one of the pad members 30 is mostly hidden.

The pad members 30 each comprise a bone contacting surface 32. The bone contacting surfaces 32 face each other and are oriented towards a respectively opposite pad holding portion 24.

As indicated in FIG. 1, the bone contacting portions 32 of the pad members 30 thus confine a clamping space CS between them. As further depicted in FIG. 1, the bone contacting surfaces 32 confine an area having a long circumferential extension C and a shorter transverse extension T, wherein said circumferential and transversal extension extend orthogonally to one another. The circumferential extension C coincides with a circumference of the clamping space CS.

Furthermore, guiding channels 34 are formed in a region between each bone contacting surface 32 and an associated pad holding portion 24. The guiding channels 34 are each provided with two openings 36 at opposite ends of the pad holding portions 24. Also, with respect to the clamping space CS and the bone contact surfaces 32, the openings 36 are located in different circumferential positions. Note that a course of a longitudinal axis L of one of the guiding channels 34 is indicated in FIG. 1. Generally, the guiding channels 34 extend in the circumferential direction along and in parallel to the bone contacting surfaces 32.

In the depicted embodiment, the surgical instrument 10 is provided for sternal closure such that a sectional axis S along which the sternum is split in half extends orthogonally through the clamping space CS.

The process of clamping sternum halves with the surgical instrument 10 is further exemplified in FIG. 2. FIG. 2 represents a schematic illustration of the surgical instrument 10 of FIG. 1, wherein for illustrative purposes the ratchet mechanism 26 is depicted with an opposite orientation, i.e., faces upwards instead of downwards.

As can be seen in FIG. 2, a sternum ST is positioned in the clamping space CS between the schematically illustrated assembly of pad members 30 and pad holding portions 24. The sternum ST is split along the sectional axis S of FIG. 1 and thus separated along a sectional area SA. As previously explained, by rotating the arms 18 about the rotational joint axis 20A, the distance between the pad members 30 can be decreased to abut against a respectively adjacent sternum halve on each side of the sectional area SA. Following that, the said sternum halves can be tightly clamped to one another.

In FIG. 2, one can further see that the circumferential extension C of the bone contacting surfaces 32 and the clamping space CS defined thereby extend substantially in parallel to an outer circumference of the sternum ST.

As further indicated in FIG. 2, a flexible elongated member 31 in form of a wire can thus be inserted into the guiding channels 34 and guided in a circumferential manner around the sternum halves to then be tensioned by connecting and twisting its free ends 33. Note that FIG. 2 illustrates the course of the wire 31 through or within the surgical instrument 10 merely schematically by a respectively dashed line. The exact position and arrangement of the wire 31 in the guiding channels 34 will be elaborated upon below.

Figure 3:
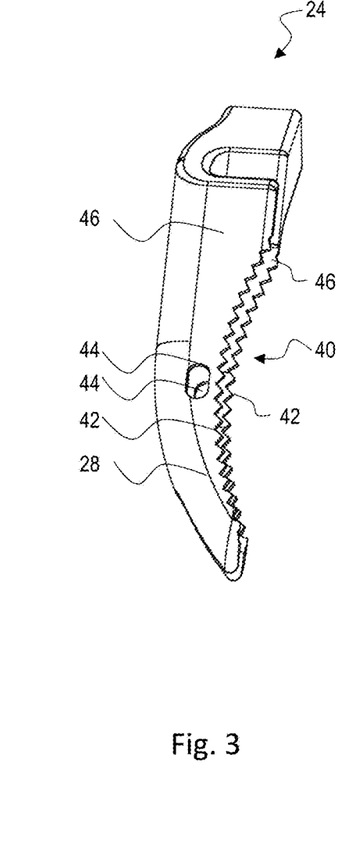
FIGS. 3 and 4 show perspective views of a pad holding portion of the surgical instrument according to the first embodiment.
Figure 4:
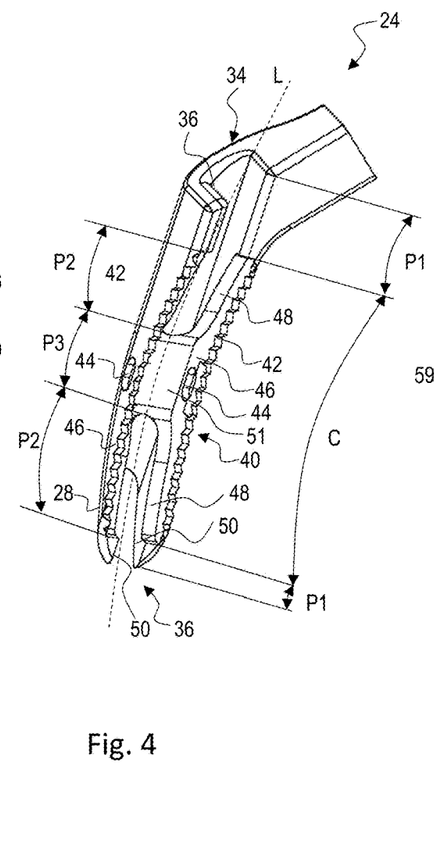

In FIGS. 3 and 4 perspective side and front views of a pad holding portion 24 of the surgical instrument 10 according to FIG. 1 are shown, without a pad member 30 being arranged therein. In FIG. 3, the curved lower end portion 28 of the pad holding portion 24 can again be seen. Furthermore, a receiving section 40 for the pad member 30 is depicted. The receiving section 40 is confined by two saw-toothed lateral edges 42 extending in the circumferential direction as defined with respect to FIGS. 1 and 2. In addition, the pad holding portion 24 comprises two openings 44 each provided in a side surface 46 of the pad holding portion 24 and being arranged opposite to and in line with one another. As can further be seen when viewing FIGS. 1 and 3 in conjunction, the side surfaces 46 extend approximately orthogonally to the bone contacting surfaces 32 when arranging a pad member 30 at the pad holding portion 24.

In FIG. 4, the openings 36 of the guiding channel 34 extending along the axis L can again be seen. In the region of the upper opening 36 of FIG. 4, the guiding channel 34 is provided with a C-shaped cross-section, so that a flexible elongated member 31 inserted therein can be surrounded on three sides. The open section of said C-shaped cross-section faces inwardly towards the oppositely arranged second pad holding portion 24 (not illustrated). At the lower opening 36 of FIG. 4, the guiding channel 34 is confined by two oppositely arranged surface sections 50 forming a slot in the pad holding portion 24. Again, the guiding channel 34 is thus provided with an inwardly opened cross-section.

Furthermore, it is shown that the receiving section 44 is specifically shaped and comprises numerous surface sections and edges for receiving and holding a pad member 30 therein. As further detailed below, the receiving section 40 is generally correspondingly shaped to a back surface 53 of the pad members 30. For example, the receiving section 40 comprises two oppositely arranged U-shaped and inclined surface sections 48 which form edges of upper and lower sidewall sections of the guiding channel 34. The surface sections 48 help to guide and secure the position of the pad members 30 within the pad holding portions 24, in particular in a circumferential direction. Furthermore, the receiving section 40 comprises a planar surface section 51 arranged in between and connecting the inclined surface sections 48. The planar surface section 51 is also positioned in the region of the openings 44 of the pad holding portion 24.

In FIG. 4, the circumferential extension C of the pad member 30 (not illustrated) as explained with regard to FIGS. 1 and 2 is again indicated. Accordingly, one can see that the length of the guiding channel 34 when extending between the openings 36 exceeds the circumferential extension C of the pad member 30. This is because in the regions of the openings 36, the guiding channel 34 is solely formed within the pad holding portion 24 as marked by the respective sections P1. These sections P1 define an additional section or length of the guiding channel 34 in the pad holding portion 24 independently of the pad member 30.

As further discussed in the following, when inserting a pad member 30 into the receiving section 40, the guiding channel 34 is jointly formed in and confined by the pad holding portion 24 and pad member 30 in the sections marked P2 in FIG. 4. Said sections P2 include the inclined surface sections 48 which abut against a correspondingly shaped back surface 53 of pad member 30. In the regions P2, the cross-section of the guiding channel 34 or, in other words, its sidewalls are thus jointly formed by the receiving section 40 of the pad holding portion 24 and a back surface 53 of a pad member 30.

On the other hand, in the central section P3 of the receiving section 40, the guiding channel 34 is formed in and confined solely by the pad member 30. As can be seen in FIG. 4, the region P3 includes the planar surface section 51 of the receiving section 40.

Again, it thus becomes apparent from FIGS. 1-4 that the guiding channel 34 extends along and largely in parallel to a bone contacting surface 32 of a pad member 30, such that a wire 31 can be directed in a circumferential manner along said pad member 30.

Figures 5, 6:
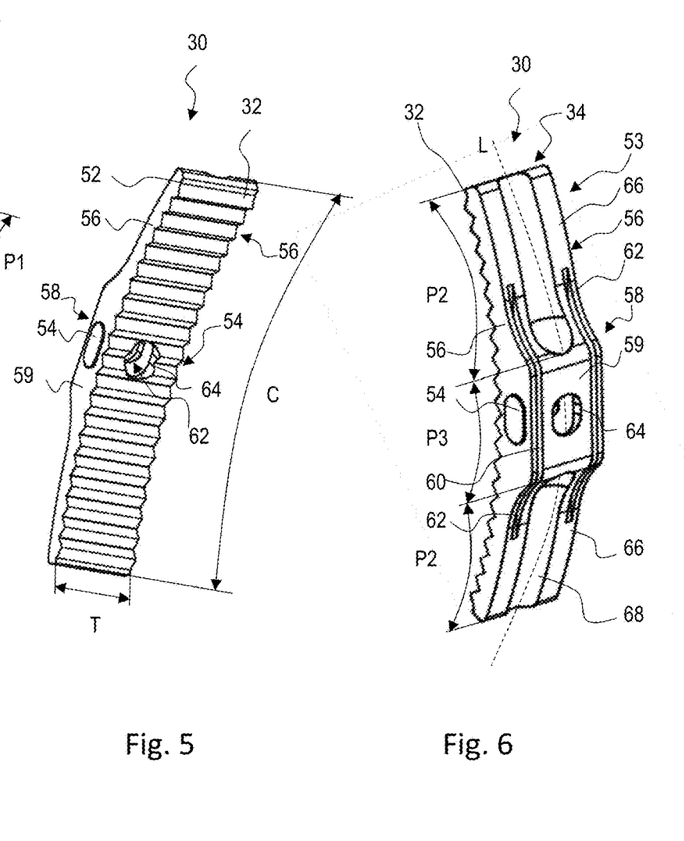
FIGS. 5-8 show perspective views of a pad member of the surgical instrument according to the first embodiment.

FIGS. 5 and 6 show perspective front and back views of a pad member 30 as used in the surgical instrument 10 according to FIG. 1. In FIG. 5, the circumferential extension C as well as the transversal extension T of the bone contacting surface 32 are once more indicated. Furthermore, one can see that the bone contacting surface 32 is provided with a plurality of regularly spaced and transversely extending grooves 52. The grooves 52 thus define a saw-toothed profile of the bone contacting surfaces 32 which, when inserted into the receiving section 40 of an associated pad holding portion 24, aligns with the saw-toothed edges 42 as explained with reference to FIG. 3. The saw-toothed profile of the bone contacting surface 32 can be beneficial in terms of avoiding damage to an adjacent bone surface. Also, it may help to increase the deformability of the pad member and thus its ability to adapt its shape to a respectively adjacent bone surface.

In FIGS. 5 and 6, it is further shown that the pad member 30 comprises a mounting portion 58 positioned at a back surface 53 of the pad member 30 and thus being generally arranged on an opposite side of the pad member 30 when compared to the bone contacting surface 32. Also, the pad member 30 has a generally curved shaped with the bone contacting surface 32 forming a curved inner side and the back surface 53 and mounting portion 58 forming a curved outer side thereof.

The mounting portion 58 is formed as substantially cuboid or block-shaped protrusion 59 which protrudes in a normal direction with reference to an adjacent region of the bone contacting surface 32.

The mounting portion 58 comprises projections 54 arranged at the side surfaces 56 of the pad member 30. Note that one of the projections 54 is hidden in the respective views of FIGS. 5 and 6. The projections 54 are formed in similar positions on both side surfaces 56 for being insertable into the openings 44 of the pad holding portion 24. Also, the shape of projections 54 is adapted to the shape of the openings 44. Accordingly, the protrusions 54 and openings 44 are configured to form a form-fit for securing the position of the pad members 30 and the pad holding portions 24.

The mounting portion 58 further comprises elastically deformable sections 60 on which the projections 54 are arranged and which form part of the side surfaces 56 of the pad member 30. The elastically deformable sections 60 are produced by providing two narrow recesses 62 at the back surface 53 of the pad member 30. The recesses 62 are arranged adjacently to the elastically deformable sections 60 and projections 54. Hence, it is possible to elastically bend the said sections 60 inwardly towards the centre of the pad member 30. Accordingly, the projections 54 can be moved inwardly when inserting the pad member 30 into the receiving section 40 to then snap-into the openings 44 for producing the desired form-fit.

For releasing the pad members 30 from the pad holding portions 24, the elastically deformable sections 60 can again be bend inwardly, for example, by pushing the protrusions 54 inwardly from outside and through the openings 44. Then, upon opening the forceps 12 and/or tensioning or pulling on the flexible elongated member 31, the pad members 30 can be released from the pad holding portions 24 and remain at the bone fragments.

FIGS. 5 and 6 further show a fixing channel 62 formed in the pad member 30. The fixing channel 62 intersects the bone contacting surface 32 and extends generally transverse thereto. The fixing channel 62 comprises two aligned openings 64, one being arranged in the bone contacting surface 32 and one at the back surface 53 of the pad member 30. As further obvious from FIGS. 5 and 6, the fixing channel 62 is arranged in a middle or central portion of the pad member 30 and adjacent to the protrusions 54. As further detailed below, the fixing channel 62 is provided to insert a fixing element 86 therein for positioning and holding the pad members 30 at a carrier member 80 prior to holding them at the forceps 12.

In FIG. 6, the course of the guiding channel 34 is again indicated by its longitudinal axis L. Furthermore, the sections P2 and P3 as explained with regard to FIG. 4 are shown. Accordingly, the pad member 30 comprises a circumferentially upper and lower section P2 in which the guiding channel 34 is jointly formed in and confined by the pad member 30 and an associated pad holding portion 24. In the sections P2, the back surface 53 is provided with an inclined surface 66 which is correspondingly shaped to the inclined surfaces 48 of the receiving section 40 as depicted in FIG. 4. Furthermore, in the sections P2 an elongated recess 68 is provided at the back surface 53 which forms a sidewall section of the guiding channel 34. When inserting the pad member 30 into the receiving section 40 of the pad holding portion 24, the inclined surfaces 48 and 66 of the pad member 30 and pad holding portion 24 thus abut against each other to jointly confine the guiding channel 34.

Also, the section P3 of the pad member 30 is indicated in which the guiding channel 34 is solely formed in a confined by the pad member 30. The section P3 includes the protrusion 59 forming the mounting portion 58. In this section, the guiding channel 34 is formed by an elongated recess forming a through-hole extending through the protrusion 59. The through-hole defines a generally closed cross-section of the guiding channel 34, except for those areas in which the fixing channel 62 and its respective openings 64 are arranged.

Figure 7:
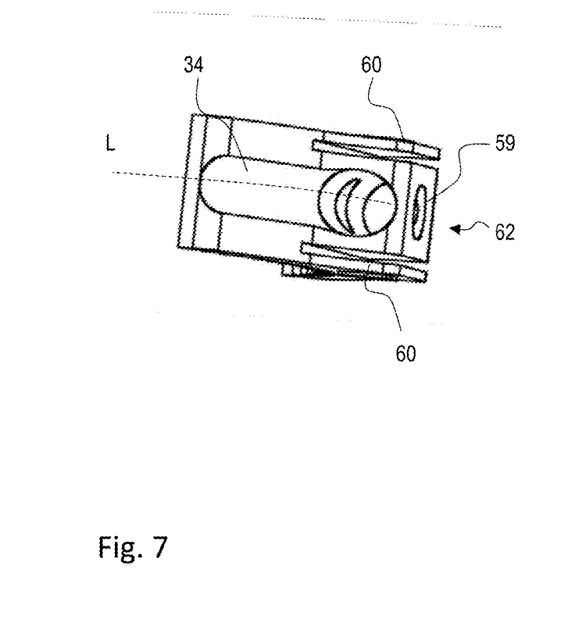

FIG. 7 shows a further perspective view of the pad member 30 depicted in FIGS. 5 and 6. Once again, the course of the guiding channel 34 is indicated by its longitudinal axis L. Furthermore, the elongated through-hole forming the guiding channel 34 within the protrusion 59 can be seen. Likewise, the elastically deformable sections 60 and the fixing channel 62 are indicated.

Figure 8:
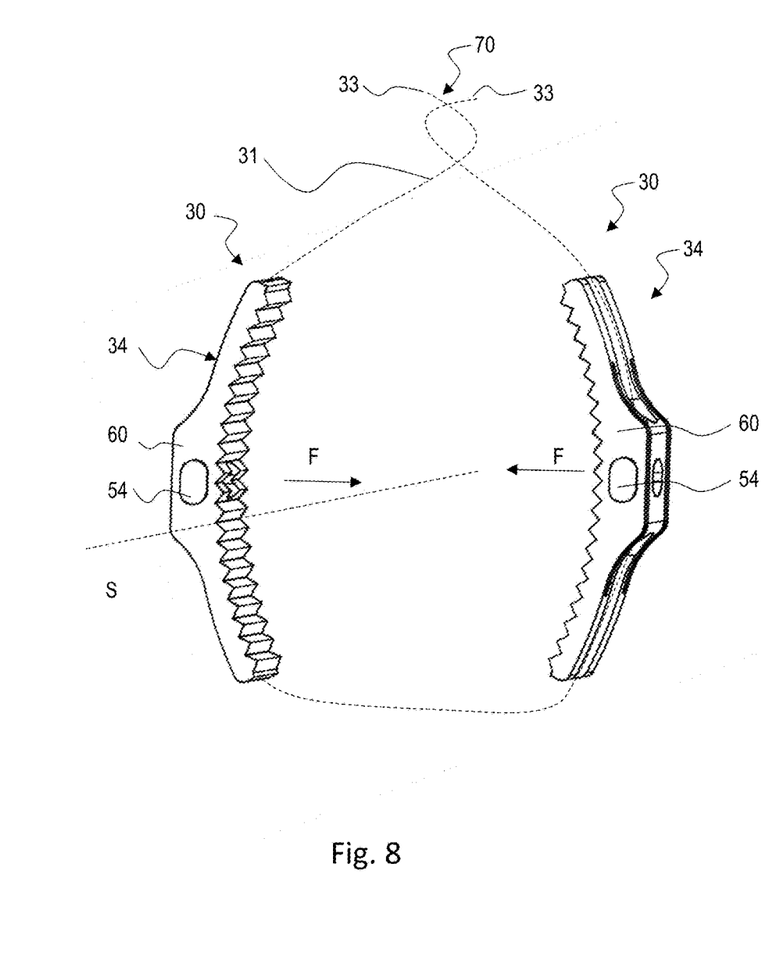

FIG. 8 depicts two pad members 30 being arranged relative to one another in a similar manner as depicted in FIGS. 1 and 2. Specifically, FIG. 8 shows a state in which the pad members 30 have been released from the pad holding portions 24 after having been positioned at oppositely arranged sternum halves ST (cf. FIG. 2). Accordingly, the sectional axis S discussed with reference to FIGS. 1 and 2 is again indicated in FIG. 8.

In FIG. 8, the flexible elongated member in form of a wire 31 is further indicated as being received and accommodated in the guiding channel sections 34 formed in the pad member 30. The free ends 33 of the wire 31 are connected to each other by twisting them to form a connection portion 70. By forming the connection portion 70, the wire 31 is circumferentially tensioned around the sectional axis S and a clamping force F is exerted onto the pad members 30 and bone fragments arranged therebetween (not illustrated). Again, it can be seen that the pad members 30 are generally arranged between the wire 31 and an adjacent bone surface (not illustrated) to avoid damage to the outer surfaces of the said bone.

Preferably, the pad members 30 are released from the pad holding portions 24 of the forceps 12 only after the connection portion 70 has been formed and the wire 31 has been tensioned. Also, as previously discussed, the forceps 12 may be used to exert a clamping force onto the bone fragments arranged between the pad members 30 and hold said clamping force prior to guiding the wire 31 through the guiding channels 34 and circumferentially around said bone fragments. The clamping force produced by the forceps 12 is then maintained until the connection portion 70 of the wire 31 is formed. In other words, the clamping effect provided by the forceps 12 is maintained until it is taken over by the wire 31.

In summary and with reference to FIGS. 1-8, this means that a primary clamping force can be provided and maintained by the forceps 12 independent of any further actions by the surgeon. The surgeon can thus focus on inserting and guiding the wire in and along the guiding channels 34 to produce the connection formation 70 as shown in FIG. 8. Afterwards, the surgeon can open the forceps 12, whereby the projections 54 of the pad members 30 slide out of the openings 44 in the pad holding portions 24 due to a deformation of the elastically deformable sections 60. Additionally or alternatively, the surgeon can pull on the wire 31 or push the protrusions 54 manually into the openings 44. Note that due to the partially open configuration of the guiding channels 34 in the sections P1 of the pad holding portions 24 as explained above, said pad holding portions 24 can be moved easily away from the pad members without being obstructed by the wire 31. In other words, the wire 31 can slide out and pass through the respectively inwardly opened regions of the guiding channels 34 in sections P1.

Figure 9:
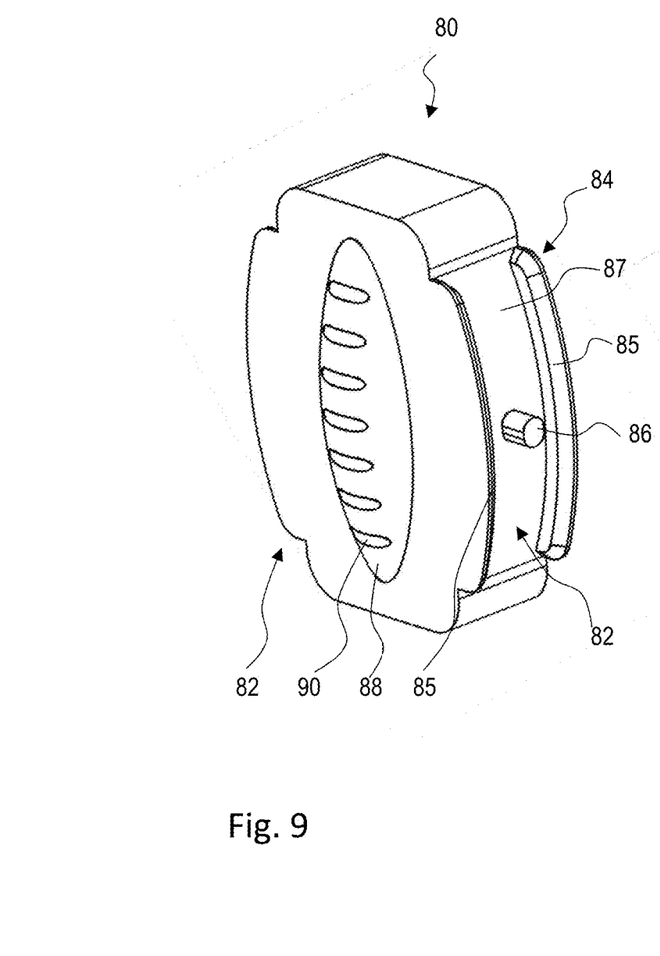
FIG. 9 shows a perspective view of a carrier member embodiment without a pad member being arranged thereon.
Figure 10:
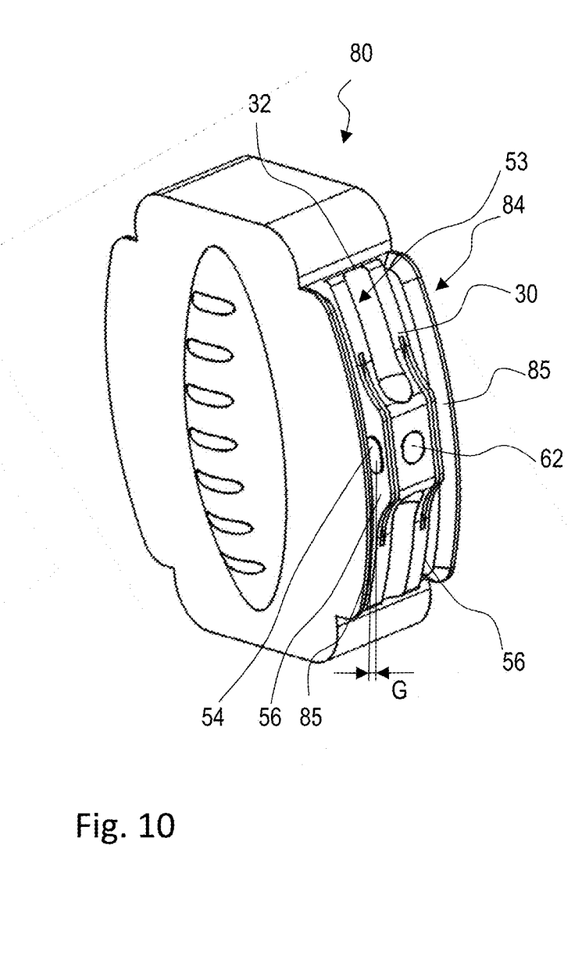
FIG. 10 shows the carrier member according to FIG. 9 with a pad member arranged thereon.

FIGS. 9 and 10 show a carrier member 80 for holding two pad members 30 prior to attaching and holding them at the pad holding portions 24 of the forceps 12 depicted in FIG. 1. The carrier members 80 are configured with two fixing portions 82 at opposite lateral sides of the carrier member 80. Note that the second fixing portion 82 is largely hidden in said figures but corresponds to the fixing portion 82 facing the viewer.

In FIG. 9, the carrier member 80 is shown without the pad members 30 being attached thereto. The carrier member 80 and in particular its fixing portions 82 are generally configured mirror-symmetrically, such that the fixing portion 82 which is hidden and faces away is similarly shaped and positioned at the carrier member 80 as the fixing portion 82 facing towards the viewer. The fixing portions 82 comprise a longitudinal recess 84 with two lateral edges 85. Furthermore, a central cylindrical protrusion 86 is provided which, as indicated by FIG. 10, extends into the fixing channel 62 of an associated pad member 30. In the state of FIG. 10, the pad members 30 are arranged so as to face outwardly with their back surfaces 53. Furthermore, the pad members 30 are generally arranged mirror-symmetrically at the carrier member 80, so that they can be easily picked-up with the forceps 12 as explained below. Note that the second pad member 30 is hidden in FIG. 10 due to being positioned at the fixing portion 82 facing away from the viewer.

As further obvious from FIG. 10, the pad member 30 is fully received in the recess 84 and surrounded along both of its side surfaces 56 by the lateral edges 85. Accordingly, the bone contacting surface 32 of the pad member 30 faces and abuts against a bottom surface 87 of the recess 84, such that it can be kept sterile and isolated from environmental influences. For improving the ease of use, the carrier member 80 is further provided with a central gripping portion 88 including several spaced apart recesses 90. The gripping portion 88 provides a save grip for manually holding the carrier member 80 when picking-up the pad members 30 with the forceps 12.

Figure 11:
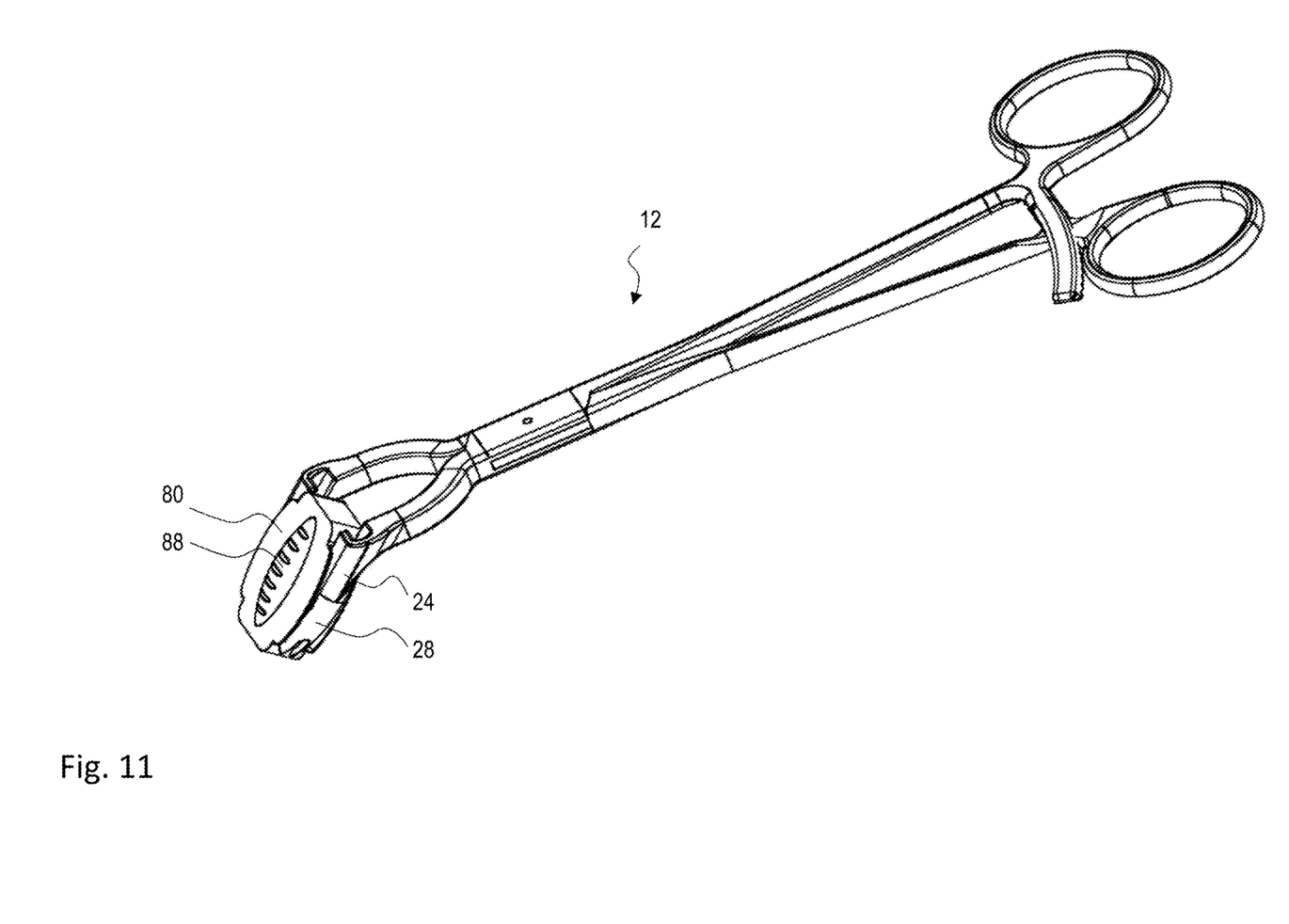
FIG. 11 shows a perspective view of a surgical kit assembly embodiment comprising a surgical instrument and carrier member.

As further indicated in FIG. 10, a gap G is formed between the projections 54 of the pad member 30 and an adjacent inner surface of the lateral edges 85. As depicted in FIG. 11, the pad holding portions 24 of the forceps can thus be positioned at the fixing portions 82 and partially inserted into the recess 84, so as to slide over and insert the back surface 53 of the pad member 30 into the receiving section 40 discussed above. This is essentially achieved by positioning the carrier member 80 between the pad holding portions 24 and then closing the forceps 12. As previously explained, this leads to the projections 54 of the pad members 30 being inserted into the openings 44 of the pad holding portions 24 to produce a form-fit. Thus, when opening the forceps 12 again, the pad members 30 are releasably held and attached at the pad holding portions 24 and can be removed from the carrier member 80. In this process, the cylindrical protrusion 86 slides out of the fixing channel 62 of the pad members 30.

Figure 12:
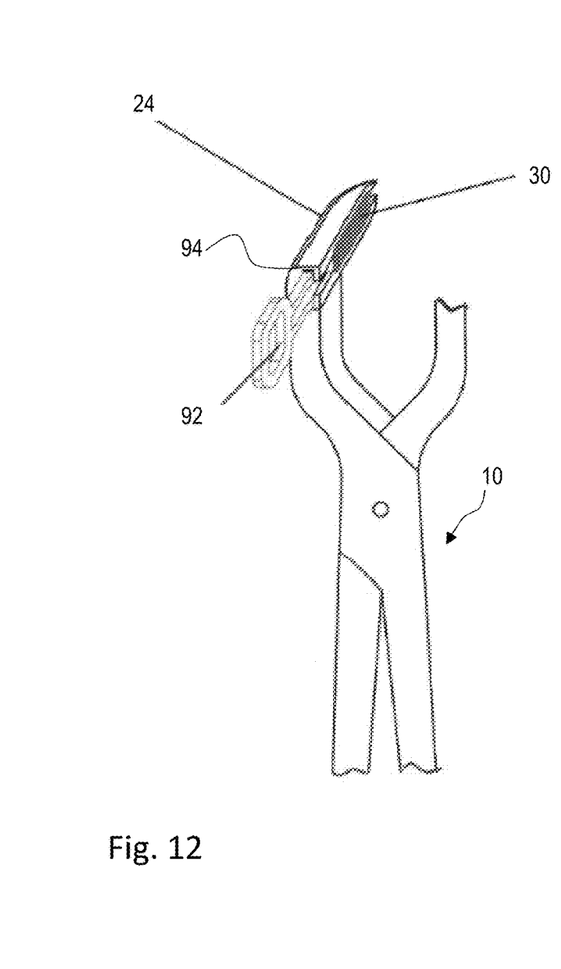
FIGS. 12-14 show various views of an embodiment of a surgical instrument comprising a securing member in form of a removable pin.
Figures 13A, 13B:
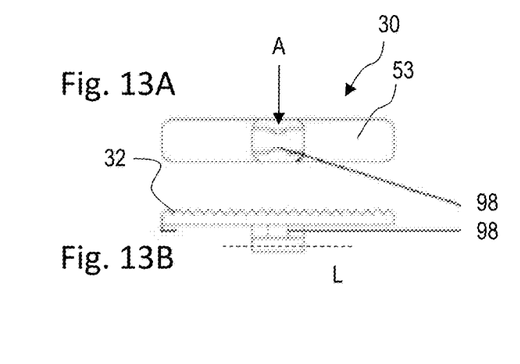
Figure 14:
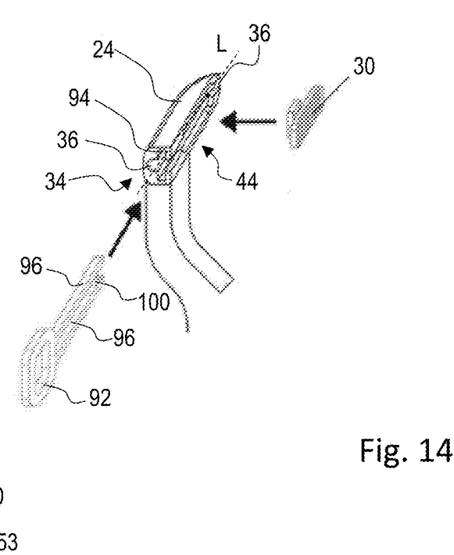

FIGS. 12-14 show a further embodiment of a surgical instrument 10 in which an additional securing member 92 in form of a removable pin is provided for temporarily fixing a pad member 30 at an associated holding portion 24. Note that Figure only shows one pad holding portion 24 and associated pad member 30. The configuration of the surgical instrument 10 is, however, substantially similar to the embodiment according to FIG. 1. The surgical instrument 10 of FIGS. 12 to 14 thus again comprises two oppositely arranged pad holding portions 24 with respective pad members 30 as well as further non-illustrated elements such as a handling portion 14 or locking mechanism 26.

In the configuration according to FIG. 12, the removable pin 42 is inserted into a guiding structure 94 within the pad holding portion 24 and secures the position of the pad member 30 within said pad holding portion 24. As shown in FIG. 14, the removable pin 92 is provided with two arms 96, wherein a distance between said arms 96 can be enlarged or decreased by elastically deforming respective sections of the removable pin 92. As further indicated in FIG. 14, the removable pin is inserted into the slot-like receiving structure 94 formed in the pad holding portion 24. Prior to that, the pad member 30 is positioned in a receiving section 44 of the pad holding portion 24.

Furthermore, FIGS. 13A and 13B show a back and side view of the pad member 30 comprising a notch 98 for receiving angled end portions 100 of the arms 96 of the removable pin 92. As indicated in FIG. 13A, said notch 98 is generally arranged at a back surface 52 of the pad member 30. Upon receiving the angled end portions 100 in said notch 98, the pad member's position in the pad holding portion 24 can be secured.

Furthermore, as indicated in FIG. 13B, the pad member 30 again comprises a mounting portion formed by a protrusion 59 which includes an elongated through-hole. Said elongated through-hole defines a section of a guiding channel 34 extending along the longitudinal axis L. As further indicated in FIG. 14, the guiding channel 34 is also partially formed within the pad holding portion 24 and defines two openings 36 at respective circumferential end portions of the pad holding portion 24.

Figure 15:
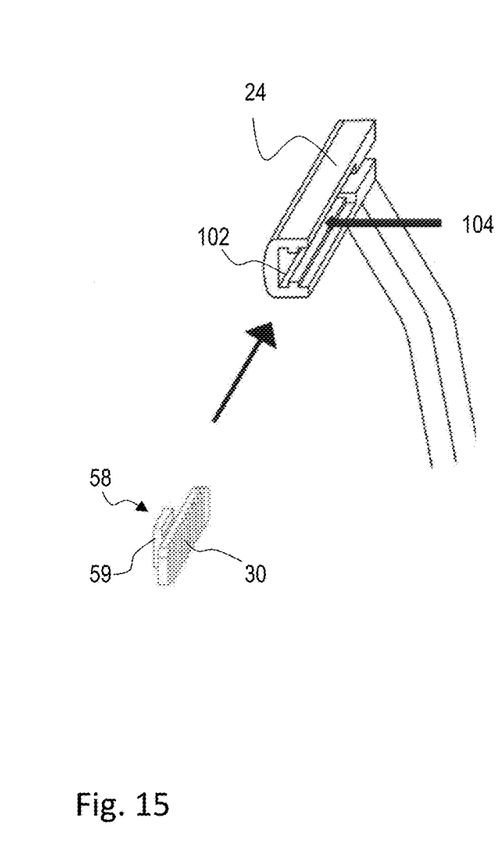
FIGS. 15-17 show various embodiments of a surgical instrument for releasably holding the pad members at associated pad holding portions.
Figure 16:
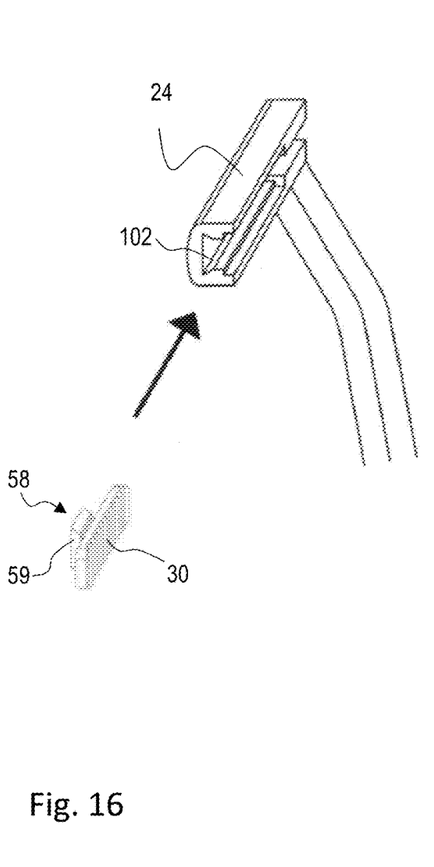
Figure 17:
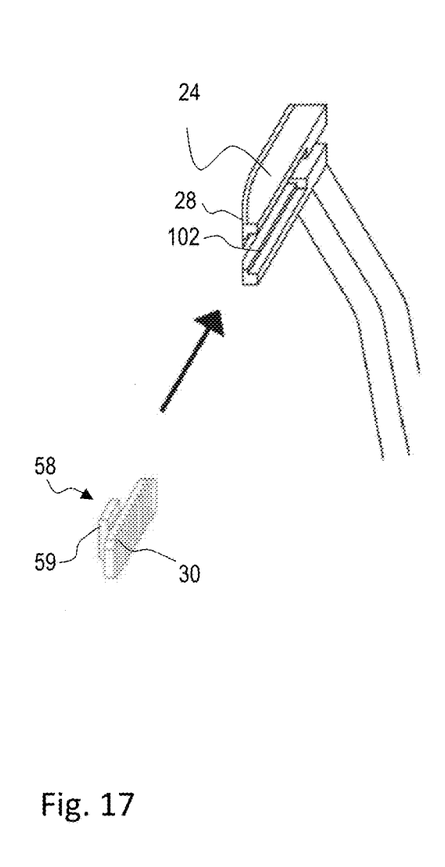

FIGS. 15-17 show further embodiments of a pad holding portion 24 comprising a pad receiving structure 102 for receiving and releasably holding a protrusion 59 of a pad member 30 therein. The protrusion 59 again forms a mounting portion 58 of the pad member 30. Note that details with regard to the guiding channel are omitted in these figures. Yet, the guiding channel can be similarly configured according to any of the previous embodiments.

In FIG. 15, the receiving structure is formed as a rectangular slot comprising an undercut region 104. In FIG. 16, the receiving structure 102 is formed so as to produce a dovetail-connection with the correspondingly shaped protrusion 59 of the pad member 30. In FIG. 17, the pad receiving structure 102 in provided as a longitudinal slot into which the protrusion 59 of the pad member 30 is inserted. Furthermore, in this example the pad holding portion 24 is provided with a curved lower end portion 28 so as to limit interferences with adjacent body parts of a patient, for example when arranging the pad holding portion 24 between the ribs of a patient during sternal closure.

Figures 18A, 18B:
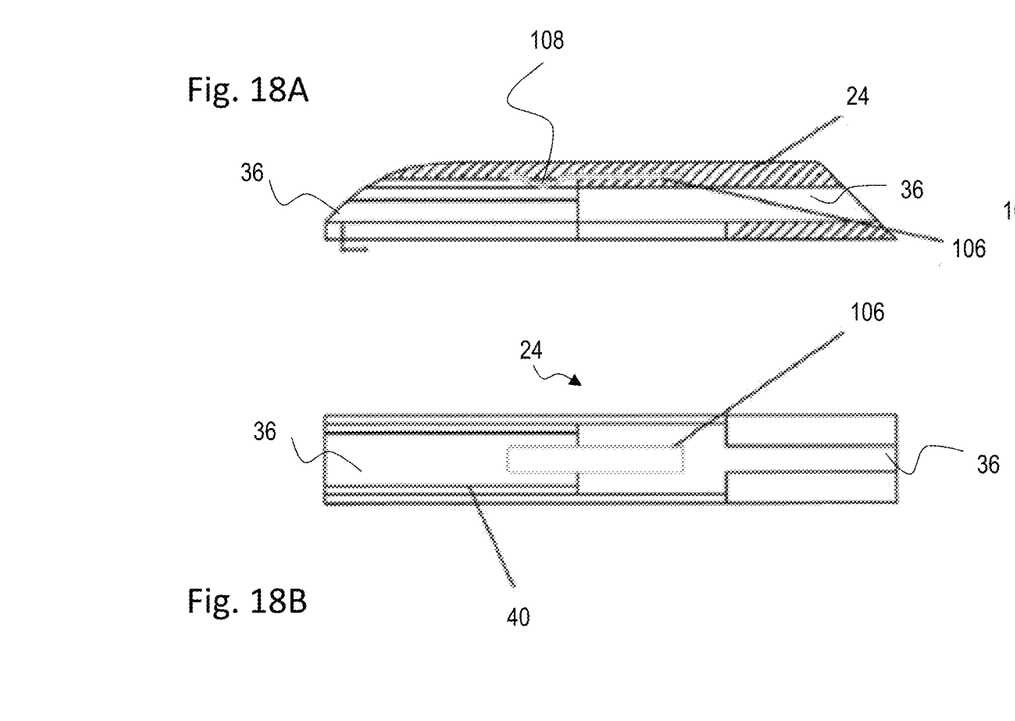
FIGS. 18A-18C show various views of an embodiment of a surgical instrument comprising a securing member in form of a spring member.
Figure 18C:
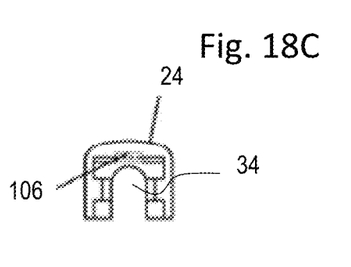

FIGS. 18A-18C show different views of a pad holding portion 24 according to a further embodiment. FIG. 18A shows a cross-sectional view through the pad holding portion 24 whereas in FIG. 18B, a receiving section 40 of the pad holding portion 24 faces towards the viewer. Furthermore, FIG. 18C shows a top view of the pad holding portion 24 and the guiding channel 34 formed therein. In this embodiment, the pad holding portion 24 comprises a securing member in form of a spring member 106. The spring member 106 comprises an engagement formation 108 for engaging a correspondingly shaped recess, undercut or the like provided in an adjacent portion of a non-illustrated pad member 30. The engagement formation 108 and a corresponding receiving structure in the pad member can thus form a snap-in connection for releasably holding the pad member 30 in the pad holding portion 24. Also, the spring member 106 may generally exert a biasing force onto the pad member 30, for example, in a clamping direction F of a respective surgical instrument 10.

The forgoing description and the accompanying drawings represent non-limiting examples of the instruments, methods and members taught herein. As such, the present invention is not limited by the forgoing description and accompanying drawings. The present invention is limited only by the following claims and their legal equivalents.

The invention claimed is:

1. A surgical instrument for fixing bone fragments, comprising:
a positioning member with two pad holding portions;
two pad members each having a bone contacting surface and each configured to be releasably held at one of the pad holding portions of the positioning member such that the bone contacting surfaces of the two pad members face each other; and
two guiding channels configured to receive a flexible elongated member, each guiding channel being formed in a region between the bone contacting surface of one of the pad members and an associated pad holding portion,
wherein the bone contacting surfaces have a circumferential extension, and each guiding channel having at least two openings which are circumferentially spaced from one another.

2. The surgical instrument according to claim 1, wherein the guiding channels extend at least partially along the associated bone contacting surface.

3. The surgical instrument according to claim 1, wherein the bone contacting surfaces each define a portion of an outer circumference of a clamping space located between the bone contacting surfaces, and each of the guiding channels has at least two openings which are arranged at different positions along the circumference of the clamping space.

4. The surgical instrument according to claim 1, wherein the bone contacting surfaces have a transversal extension, with the circumferential extension exceeding the transversal extension.

5. The surgical instrument according to claim 1, wherein the guiding channels comprise at least one section which is configured with a closed cross-section.

6. The surgical instrument according to claim 1, wherein the guiding channels have a length of at least 5 millimeters.

7. The surgical instrument according to claim 1, wherein a largest cross-sectional extension of the guiding channels is below 5 centimeters.

8. The surgical instrument according to claim 1, wherein the guiding channels are at least partially formed in the pad members.

9. The surgical instrument according to claim 1, wherein the guiding channels are at least partially formed in the positioning member.

10. The surgical instrument according to claim 1, wherein the guiding channels comprise an elongated through-hole.

11. The surgical instrument according to claim 1, wherein the positioning member is configured to move at least one of the bone contacting surfaces towards the other to exert a clamping force.

12. The surgical instrument according to claim 11, wherein the positioning member is configured to arrange the bone contacting surfaces a defined distance from one another and to hold the defined distance upon exerting a clamping force.

13. The surgical instrument according to claim 1, wherein the positioning member is a forceps and the pad holding portions are formed in tip regions of the forceps.

14. The surgical instrument according to claim 1, wherein the pad members are releasably held by means of at least one of a form-fit and a press fit.

15. The surgical instrument according to claim 1, wherein at least one of the pad members is configured with a mounting portion to be releasably inserted into a receiving section of an associated pad holding portion.

16. The surgical instrument according to claim 15, wherein the mounting portion and the bone contacting surface are arranged on opposite sides of the of the pad member.

17. The surgical instrument according to claim 1, wherein at least one of the pad members has a generally curved main part with the bone contacting surface arranged on an inner side of the curved main part and the mounting portion on an outer side of the curved main part.

18. The surgical instrument according to claim 1, wherein the surgical instrument further comprises at least one securing member for temporarily securing at least one of the pad members at the positioning member and for releasing the pad member from the positioning member upon operating the securing member.

19. A surgical instrument for fixing bone fragments, comprising:
a tip region with two opposing pad holding portions;

two pad members each having a bone contacting surface and each configured to be releasably coupled to one of the pad holding portions such that the bone contacting surfaces of the two pad members face each other; and two guiding channels configured to receive a flexible elongated member, each guiding channel being formed in a region between one of the pad members coupled to a respective pad holding portion, wherein the bone contacting surfaces each define a portion of an outer circumference of a clamping space located between the bone contacting surfaces, and each of the guiding channels has at least two openings which are arranged at different positions along the circumference of the clamping space.

20. A surgical instrument for fixing bone fragments, comprising:

two pad holding portions;

two pad members releasably coupled to one of the pad holding portions such that bone contacting surfaces of the two pad members face each other; and two guiding channels configured to receive a flexible elongated member, each guiding channel being formed in a region between one of the pad members and an associated pad holding portion, wherein each of the two guiding channels comprise at least one section which is configured with a closed cross-section such that the flexible elongated member is inserted through and housed within the closed cross-section.

21. A surgical kit assembly, comprising:

a flexible elongated member; and a surgical instrument having a positioning member, two pad members and two guiding channels, wherein the positioning member includes two pad holding portions, wherein the two pad members each include a bone contacting surface and each configured to be releasably held at one of the pad holding portions of the positioning member such that the bone contacting surfaces of the two pad members face each other, and wherein the two guiding channels are configured to receive the flexible elongated member, each guiding channel being formed in a region between the bone contacting surface of one of the pad members and an associated pad holding portion, wherein the bone contacting surfaces have a circumferential extension, and each guiding channel having at least two openings which are arranged at different positions along the circumferential extension.

22. The surgical kit assembly according to claim 21, further comprising:

a carrier member for releasably carrying the pad members prior to holding them at the positioning member.

23. The surgical kit assembly of claim 22, wherein the pad members each include a mounting portion which are arranged on opposite sides of the pad members, the pad members being arranged on opposite sides of the carrier member with each of the bone contacting surfaces facing an associated fixing portion of the carrier member.

24. The surgical kit assembly according to claim 21, wherein the pad members each include a mounting portion which are arranged on opposite sides of the pad members, the mounting portions including at least one protrusion comprising an elongated recess, the elongated recess forming the guiding channels.

25. A method for fixing bone fragments, comprising the steps of:

a) releasably holding a pad member at each of two pad holding portions of a positioning member;

b) positioning the pad members at bone fragments by means of the positioning member, such that bone contacting surfaces of the pad members contact the bone fragments, the bone contacting surfaces each defining a portion of an outer circumference of a clamping space located between the bone contacting surfaces;

c) arranging a flexible elongated member in guiding channels, each guiding channel extending in a region between the bone contacting surface of one of the pad members and an associated pad holding portion, each of the guiding channels having at least two openings which are arranged at different positions along the circumference of the clamping space;

d) tensioning the flexible elongated member around said bone fragments, such that the pad members are at least partially arranged between the flexible elongated member and the bone fragments;

e) releasing the pad members from the positioning member;

f) removing the positioning member.

* * * * *